United States Patent
Obendorf et al.

(10) Patent No.: US 7,208,283 B2
(45) Date of Patent: Apr. 24, 2007

(54) METHODS FOR DETERMINING HORMONAL EFFECTS OF SUBSTANCES USING EWING SARCOMA PROTEIN AND ANDROGEN RECEPTOR

(75) Inventors: Maik Obendorf, Weimar (DE); Siegmund Wolf, Bad Klosterlausnitz (DE)

(73) Assignee: Bayer Schering Pharma AG, Berlin (DE)

( * ) Notice: Subject to any disclaimer, the term of this patent is extended or adjusted under 35 U.S.C. 154(b) by 0 days.

(21) Appl. No.: 10/791,017

(22) Filed: Mar. 2, 2004

(65) Prior Publication Data

US 2004/0197827 A1    Oct. 7, 2004

Related U.S. Application Data

(60) Provisional application No. 60/465,692, filed on Apr. 25, 2003.

(30) Foreign Application Priority Data

Mar. 4, 2003    (DE) ................ 103 09 280

(51) Int. Cl.
  *G01N 33/567* (2006.01)
  *C07K 14/72* (2006.01)
  *C12N 5/16* (2006.01)
  *C12N 15/09* (2006.01)
  *C12N 15/63* (2006.01)

(52) U.S. Cl. .............. 435/7.21; 435/69.1; 435/325; 435/375; 435/455; 530/350

(58) Field of Classification Search .......... 435/7.2
  See application file for complete search history.

(56) References Cited

U.S. PATENT DOCUMENTS

2003/0082511 A1* 5/2003 Brown et al. ............ 435/4

FOREIGN PATENT DOCUMENTS

WO    99/50664    10/1999
WO    02/36621 A1    5/2002

OTHER PUBLICATIONS

Wells (Sep. 18, 1990) "Additivity of Mutational Effects in Proteins." Biochemistry 29(37): 8509-8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Bork (2000) "Powers and Pitfalls in Sequence Analysis: The 70% Hurdle." Genome Research 10:398-400.*
Skolnick and Fetrow (2000) "From gene to protein structure and function: novel applications of computational approaches in the genomic era." Trends in Biotech. 18(1): 34-39.*
Doerks et al. (Jun. 1998) "Protein annotation: detective work for function prediction." Trends in Genetics 14(6): 248-250.*
Smith and Zhang (Nov. 1997) "The challenges of genome sequence annotation or 'The devil is in the details'." Nature Biotechnology 15:1222-1223.*
Brenner (Apr. 1999) "Errors in genome annotation." Trends in Genetics 15(4): 132-133.*
Bork and Bairoch (Oct. 1996) "Go hunting in sequence databases but watch out for the traps." Trends in Genetics 12(10): 425-427.*
Heinlein, et al. Endocrine Reviews. 23(2): 175-200.*
GenBank Accession No. AAA51775, NCBI Protein Database, published Feb. 11, 2002.*
Databank Pubmed BEI NCBI, Adresse www.NCBI,NLM,NIH.gov, Zusammenfassung Zu: Thomas et al: The Pro-Oncoprotein . . . , in Cancer Biol. Ther (2002) 1 (4), 428-32.
Vishwanie Budhram-Mahaseo, et al: "Pou Transcription Factors BRN-3A . . . " in Molecular and Cellular Biology, Feb. 1998, vol. 18, No. 2, p. 1029-1041.
Annie Maltais et al: "The AF2 Domain of the Orphan Nuclear Receptor . . . ", in Cancer Letter 183, 2002, pp. 87-94.
Naganari Ohkura et al: "The EWS/NOR1 Fusion Gene . . . " in the Journal of Biological Chemistry, vol. 277, No. 1, Issue of Jan. 4, pp. 535-543, 2002.
Mira A Rao et al: "RANBPM, A Nuclear Protein That Interacts . . . " in the Journal of Biological Chemistry, vol. 277, No. 50, Issue of Dec. 2002, pp. 48020-48027.
Daniel Robyr, et al: "Nuclear Hormone Receptor . . ", in Molecular Endocrinology, vol. 14, No. 3, 2000, pp. 329-347.
Ana Aranda et al: "Nuclear Hormone Receptors and Gene Expression" in Physiological Reviews, vol. 81, No. 3, Jul. 2001, pp. 1269-1304.
M. Beato et al: "Steroid Hormone Receptors: An Update" in Human Reproduction Update 2000, vol. 6, No. 3, pp. 225-236.
David J. Mangelsdorf: "The RXR Heterodimers . . . " in Cell, vol. 83, Dec. 15, 1995, pp. 841-850.

(Continued)

Primary Examiner—Elizabeth Kemmerer
Assistant Examiner—Zachary C. Howard
(74) Attorney, Agent, or Firm—Michael J. Striker

(57) ABSTRACT

In the method of determining hormonal effects of substances, a test substance is contacted with Ewing sarcoma protein (EWS) or a derivative of it and with an androgen receptor (NR) or a derivative of it; and the effect of the test substance on binding of EWS with the androgen receptor or its derivative or on ligand-induced activity of the androgen receptor is determined, preferably in a cellular system. A method for determining interference in the co-modulator mechanism between androgen receptor and EWS, which includes measurement of androgen receptor and EWS concentrations, is described. A method for identification and characterization of substances that influence the activity of a nuclear receptor, especially androgen receptor, using EWS or a derivative of it is disclosed.

10 Claims, 8 Drawing Sheets

OTHER PUBLICATIONS

A.O. Brinkmann et al: "Mechanism of Androgen Receptor . . . " in Journal of Steroid Biochemistry and Molecular Biology 69, 1999, pp. 307-313.

Olivier Delattre et al: "Gene Fusion With an ETS DNA . . . " in Letters to Nature, vol. 359, Sep. 10, 1992, pp. 162-165.

Jessica Zucman et al: "EWS and ATF-1 Gene Fusion . . . " in Nature Genetics vol. 4, Aug. 1993, pp. 341-345.

William L. Gerald et al: "Characterization of the Genomic Beakpoint . . . " in Proc. Natl. Acad. SCI. USA, vol. 92, Feb. 1995, pp. 1028-1032.

Yves Labelle et al: "Oncogenic Coversion of a Novel Orphan . . . " in Human Molecular Genetics, vol. 4, No. 12, 1995, pp. 2219-2226.

Takatoshi Ohno et al: "The EWS Gene, Involed in Ewing Family . . . " in Oncogene 1994, 9, pp. 3087-3097.

Thomas Melot et al: "Characterization of a New Bran-Specific . . . " in Eur. J. Biochem. 268, 2001, pp. 3483-3489.

Neil J. McKenna et al: "Nuclear Receptor Coregulators . . . " in Endocrine Reviews 20(3), 1999, pp. 321-344.

Xui Fen Ding et al: "Nuclear Receptor-Binding Sites of . . . " in Molecular Endocrinology, 1998, pp. 302-313.

Araya Natsumi et al: "Cooperative Interaction of . . . " Journal of Biological Chemistry, vol. 278, No. 7, Issue of Feb. 14, 2003, pp. 5427-5432.

Felsch Jason et al: "Tyrosine Kinase . . . " Current Biology, Bd. 9, Nr. 9, May 6, 1999, pp. 485-488.

Vermeulen A. et al: "Diagnosis of Hypogonadism in the Aging Male" Aging Male 2002 United Kingdom, Bd. 5, Nr. 3, 2002, pp. 170-176.

David M. Heery, et al: "A Signature Motif in Transcriptional Co-Activators . . . " in Nature, vol. 387, Jun. 12, 1997. (In English).

Xin Wang et al: "Identification and Characterization of a Novel . . . " The Journal of Biological Chemistry, vol. 276, No. 44, Issue of Nov. 2, 2001, pp. 40417-40423. (In English).

Naohiro Fujimoto et al: "Cloning and Characterization . . . " Journal of Biological Chemistry, vol. 274, No. 12, Issue of Mar. 19, 1999, pp. 8316-8321. (In English).

Hong-Yo Kang et al: Cloning and Characterization of Human Prostate . . . : The Journal of Biological Chemistry, vol. 274, No. 13, Issue of Mar. 26, 1999, pp. 8670-8576. (In English).

Anu-Maarit Moilanen et al: "A Testis-Specific Androgen Receptor . . . " The Journal of Biological Chemistry, vol. 274, No. 6, Issue of Feb. 5, 1999, pp. 3700-3704. (In English).

Anu-Maarit Moilanen et al: "Identification of a Novel Ring Finger . . . " Molecular and Cellular Biology, Sep. 1998, vol. 18, No. 9, pp. 5128-5139.

Kazuo Nishimura et al: "Modulation of Androgen Receptor . . . " Cancer Research 63, Aug. 15, 2003, pp. 4888-4894. (In English).

Hetti Poukkat et al: "UBC9 Interacts With The . . . " The Journal of Biological Chemistry, vol. 274, No. 27, Issue of Jul. 2, 1999, pp. 19441-19446. (In English).

* cited by examiner

FIG. 3

```
  1 agagggagac ggacgttgag agaacgagga ggaaggagag aaaATGGCGT CCACGGATTA
                                                        M  A  S  T  D
                                                                   >>>>
>>>>>>>>>>>>>>>>>>>>>>>>>>>>>exon 1>>>>>>>>>>>>>>>>>>>>>>>>>>>>

61 CAGTACCTAT AGCCAAGCTG CAGCGCAGCA GGGCTACAGT GCTTACACCG CCCAGCCCAC
     Y  S  T  Y  S  Q  A  A  A  Q  Q  G  Y  S  A  Y  T  A  Q  P
    >>>>>>>>>>>>>exon 2>>>>>>>>>>>>>>>
                                 >>>>>>>>>>>>>exon 3>>>>>>>>>>>

121 TCAAGGATAT GCACAGACCA CCCAGGCATA TGGGCAACAA AGCTATGGAA CCTATGGACA
     T  Q  G  Y  A  Q  T  T  Q  A  Y  G  Q  Q  S  Y  G  T  Y  G
                              >>>>>>>>>>>>>>>>exon 4>>>>>>>>>>>>>>>>
    >>>>>>>>>>exon 3>>>>>>>>>>>

181 GCCCACTGAT GTCAGCTATA CCCAGGCTCA GACCACTGCA ACCTATGGGC AGACCGCCTA
     Q  P  T  D  V  S  Y  T  Q  A  Q  T  T  A  T  Y  G  Q  T  A
    >>>>>>>>>>>>>>>>>>>>>>>>>>>>>>>exon 4>>>>>>>>>>>>>>>>>>>>>>>>>>>>>

241 TGCAACTTCT TATGGACAGC CTCCCACTGG TTATACTACT CCAACTGCCC CCCAGGCATA
     Y  A  T  S  Y  G  Q  P  P  T  G  Y  T  T  P  T  A  P  Q  A
                              >>>>>>>>>>>>>exon 5>>>>>>>>>>>>>>>>
    >>>>>>>>>>>>exon 4>>>>>>>>>>>>>

301 CAGCCAGCCT GTCCAGGGGT ATGGCACTGG TGCTTATGAT ACCACCACTG CTACAGTCAC
     Y  S  Q  P  V  Q  G  Y  G  T  G  A  Y  D  T  T  T  A  T  V
    >>>>>>>>>>>>>>>>>>>>>>>>>>>>>>>exon 5>>>>>>>>>>>>>>>>>>>>>>>>>>>>>

361 CACCACCCAG GCCTCCTATG CAGCTCAGTC TGCATATGGC ACTCAGCCTG CTTATCCAGC
     T  T  T  Q  A  S  Y  A  A  Q  S  A  Y  G  T  Q  P  A  Y  P
    >>>>>>>>>>>>>>>>>>>>>>>>>>>>>>>exon 5>>>>>>>>>>>>>>>>>>>>>>>>>>>>>

421 CTATGGGCAG CAGCCAGCAG CCACTGCACC TACAAGACCG CAGGATGGAA ACAAGCCCAC
     A  Y  G  Q  Q  P  A  A  T  A  P  T  R  P  Q  D  G  N  K  P
                                           >>>>>>>>>>exon 6>>>>>>>>>>
    >>>>>>>>>>>>>>>>exon 5>>>>>>>>>>>>>>>>

481 TGAGACTAGT CAACCTCAAT CTAGCACAGG GGGTTACAAC CAGCCCAGCC TAGGATATGG
     T  E  T  S  Q  P  Q  S  S  T  G  G  Y  N  Q  P  S  L  G  Y
    >>>>>>>>>>>>>>>>>>>>>>>>>>>>>exon 6>>>>>>>>>>>>>>>>>>>>>>>>>>>>>

541 ACAGAGTAAC TACAGTTATC CCCAGGTACC TGGGAGCTAC CCCATGCAGC CAGTCACTGC
     G  Q  S  N  Y  S  Y  P  Q  V  P  G  S  Y  P  M  Q  P  V  T
    >>>>>>>>>>>>>>>>>>>>>>>>>>>>>exon 6>>>>>>>>>>>>>>>>>>>>>>>>>>>>>
```

```
 601  ACCTCCATCC TACCCTCCTA CCAGCTATTC CTCTACACAG CCGACTAGTT ATGATCAGAG
       A  P  P  S  Y  P  P  T  S  Y  S  S  T  Q  P  T  S  Y  D  Q
                                     >>>>>>>>>>>>>>>>>exon 7>>>>>>>>>>>>>>>
      >>>>>>>>>exon 6>>>>>>>>>>>

661  CAGTTACTCT CAGCAGAACA CCTATGGGCA ACCGAGCAGC TATGGACAGC AGAGTAGCTA
       S  S  Y  S  Q  Q  N  T  Y  G  Q  P  S  S  Y  G  Q  Q  S  S
      >>>>>>>>>>>>>>>>>>>>>>>>>>>>>>>exon 7>>>>>>>>>>>>>>>>>>>>>>>>>>>>>>>

721  TGGTCAACAA AGCAGCTATG GGCAGCAGCC TCCCACTAGT TACCCACCCC AAACTGGATC
       Y  G  Q  Q  S  S  Y  G  Q  Q  P  P  T  S  Y  P  P  Q  T  G
      >>>>>>>>>>>>>>>>>>>>>>>>>>>>>>>exon 7>>>>>>>>>>>>>>>>>>>>>>>>>>>>>>>

781  CTACAGCCAA GCTCCAAGTC AATATAGCCA ACAGAGCAGC AGCTACGGGC AGCAGAGTTC
       S  Y  S  Q  A  P  S  Q  Y  S  Q  Q  S  S  S  Y  G  Q  Q  S
                                                                    >>>>
      >>>>>>>>>>>>>>>>>>>>>>>>>>>>>>>exon 7>>>>>>>>>>>>>>>>>>>>>>>>>>>>>

841  ATTCCGACAG GACCACCCCA GTAGCATGGG TGTTTATGGG CAGGAGTCTG GAGGATTTTC
       S  F  R  Q  D  H  P  S  S  M  G  V  Y  G  Q  E  S  G  G  F
      >>>>>>>>>>>>>>>>>>>>>>>>>>>>>>>exon 8>>>>>>>>>>>>>>>>>>>>>>>>>>>>>>>

901  CGGACCAGGA GAGAACCGGA GCATGAGTGG CCCTGATAAC CGGGGCAGGG GAAGAGGGGG
       S  G  P  G  E  N  R  S  M  S  G  P  D  N  R  G  R  G  R  G
      >>>>>>>>>>>>>>>>>>>>>>>>>>>>>>>exon 8>>>>>>>>>>>>>>>>>>>>>>>>>>>>>>>

961  ATTTGATCGT GGAGGCATGA GCAGAGGTGG GCGGGGAGGA GGACGCGGTG GAATGGGCAG
       G  F  D  R  G  G  M  S  R  G  G  R  G  G  G  R  G  G  M  G
                                                                    >>>
      >>>>>>>>>>>>>>>>>>>>>>>>>>>>>>>exon 8>>>>>>>>>>>>>>>>>>>>>>>>>>>>>>>

1021  CGCTGGAGAG CGAGGTGGCT TCAATAAGCC TGGTGGACCC ATGGATGAAG GACCAGATCT
       S  A  G  E  R  G  G  F  N  K  P  G  G  P  M  D  E  G  P  D
                                              >>>>>>>>>>>exon 10>>>>>>>>>>
      >>>>>>>>>>>>>>>>exon 9>>>>>>>>>>>>>>>>

1081  TGATCTAGGC CCACCTGTAG ATCCAGATGA AGACTCTGAC AACAGTGCAA TTTATGTACA
       L  D  L  G  P  P  V  D  P  D  E  D  S  D  N  S  A  I  Y  V
                     >>>>>>>>>>>>>>>>>>>>>>>>>>>exon 11>>>>>>>>>>>>>>>>>>>>
      >>>>>>>>>

1141  AGGATTAAAT GACAGTGTGA CTCTAGATGA TCTGGCAGAC TTCTTTAAGC AGTGTGGGGT
       Q  G  L  N  D  S  V  T  L  D  D  L  A  D  F  F  K  Q  C  G
      >>>>>>>>>>>>>>>>>>>>>>>>>>>>>>>exon 11>>>>>>>>>>>>>>>>>>>>>>>>>>>>>>
```

```
1201  TGTTAAGATG AACAAGAGAA CTGGGCAACC CATGATCCAC ATCTACCTGG ACAAGGAAAC
       V  V  K  M   N  K  R   T  G  Q   P  M  I  H   I  Y  L    D  K  E
            >>>>>>>>>>>>>>>>>>>>>>>>>>>>>exon 12>>>>>>>>>>>>>>>>>>>>>>>>>
      >>>>>>>

1261  AGGAAAGCCC AAAGGCGATG CCACAGTGTC CTATGAAGAC CCACCCACTG CCAAGGCTGC
       T  G  K  P   K  G  D   A  T  V   S  Y  E  D   P  P  T   A  K  A
      >>>>>>>>>>>>>>>>>>>>>>>>>>>>>>>>exon 12>>>>>>>>>>>>>>>>>>>>>>>>>>>>

1321  CGTGGAATGG TTTGATGGGA AAGATTTTCA AGGGAGCAAA CTTAAAGTCT CCCTTGCTCG
       A  V  E  W   F  D  G   K  D  F   Q  G  S  K   L  K  V   S  L  A
                    >>>>>>>>>>>>>>>>>>>>exon 13>>>>>>>>>>>>>>>>>>>>>>>
      >>>>>exon 12>>>>>>

1381  GAAGAAGCCT CCAATGAACA GTATGCGGGG TGGTCTGCCA CCCCGTGAGG GCAGAGGCAT
       R  K  K  P   P  M  N   S  M  R   G   G  L   P  P  R  E   G  R  G
      >>>>>>>>>>>>>>>>>>>>>>>>>>>>>>>>exon 13>>>>>>>>>>>>>>>>>>>>>>>>>>>>

1441  GCCACCACCA CTCCGTGGAG GTCCAGGAGG CCCAGGAGGT CCTGGGGGAC CCATGGGTCG
       M  P  P  P   L  R  G   P  G  G   P  G  G   P  G  G   P  M  G
                         >>>>>>>>>>>>>>>>>>exon 14>>>>>>>>>>>>>>>>>>>>
      >>>>>>exon 13>>>>>>>>>

1501  CATGGGAGGC CGTGGAGGAG ATAGAGGAGG CTTCCCTCCA AGAGGACCCC GGGGTTCCCG
       R  M  G  G   R  G  G   D  R  G   G  F  P  P   R  G  P   R  G  S
      >>>>>>>>>>>>>>>>>>>>>>>>>>>>>>>>exon 14>>>>>>>>>>>>>>>>>>>>>>>>>>>>

1561  AGGGAACCCC TCTGGAGGAG GAAACGTCCA GCACCGAGCT GGAGACTGGC AGTGTCCCAA
       R  G  N  P   S  G  G   G  N  V   Q  H  R  A   G  D  W   Q  C  P
      >>>>>>>>>>>>>>>>>>>>>>>>>>>>>>>exon 14>>>>>>>>>>>>>>>>>>>>>>>>>>>>>

1621  TCCGGGTTGT GGAAACCAGA ACTTCGCCTG GAGAACAGAG TGCAACCAGT GTAAGGCCCC
       N  P  G  C   G  N  Q   N  F  A   W  R  T  E   C  N  Q   C  K  A
             >>>>>>>>>>>>>exon 15b>>>>>>>>>>>>>>>>>>>>>>>>>>>>
             >>>>>>>>>>>>>>>>>>>>>>>>>>exon 15>>>>>>>>>>>>>>>>>>>>>>>>>>>
      >>>

1681  AAAGCCTGAA GGCTTCCTCC CGCCACCCTT TCCGCCCCCG GGTGGTGATC GTGGCAGAGG
       P  K  P  E   G  F  L   P  P  P   F  P  P  P   G  D  R   G  R
                                                         >>>>>>>exon 16>>>>>>
      >>>>>>>>>>>>>>>>exon 15>>>>>>>>>>>>>>>>>>>>>
```

```
1741  TGGCCCTGGT GGCATGCGGG GAGGAAGAGG TGGCCTCATG GATCGTGGTG GTCCCGGTGG
       G  G  P    G  M  R    G  R      G  G  L  M   D  R  G    G  P  G
      >>>>>>>>>>>>>>>>>>>>>>>>>>>>>>>>>exon 16>>>>>>>>>>>>>>>>>>>>>>>>>>>>>

1801  AATGTTCAGA GGTGGCCGTG GTGGAGACAG AGGTGGCTTC CGTGGTGGCC GGGGCATGGA
       G  M  F    R  G  G    G  D      R  G  G  F  R  G  G    R  G  M
      >>>>>>>>>>>>>>>>>>>>>>>>>>>>>>>>>exon 16>>>>>>>>>>>>>>>>>>>>>>>>>>>>>

1861  CCGAGGTGGC TTTGGTGGAG GAAGACGAGG TGGCCCTGGG GGGCCCCCTG GACCTTTGAT
       D  R  G  G  F  G  G   G  R  R    G  G  P  G  G  P  P   G  P  L
      >>>>>>>>>>>>>>>>>>>>>>>>>>>>>>>>>exon 16>>>>>>>>>>>>>>>>>>>>>>>>>>>>>

1921  GGAACAGATG GGAGGAAGAA GAGGAGGACG TGGAGGACCT GGAAAAATGG ATAAAGGCGA
       M  E  Q  M  G  G  R   R  G      R  G  P    G  K  M    D  K  G
                                                                      >>>>>>
      >>>>>>>>>>>>>>>>>>>>>>>>>>>>exon 16>>>>>>>>>>>>>>>>>>>>>>>>>>>

1981  GCACCGTCAG GAGCGCAGAG ATCGGCCCTA Ctagatgcag agacccgca gagctgcatt
       E  H  R  Q  E  R  R   D  R  P   Y  stop
      >>>>>>>>>>>>>>>>>>>>>>>>>>>>>>>>>exon 17>>>>>>>>>>>>>>>>>>>>>>>>>>>>>

2041  gactaccaga tttatttttt aaaccagaaa atgttttaaa tttataattc catatttata
      >>>>>>>>>>>>>>>>>>>>>>>>>>>>>>>>>exon 17>>>>>>>>>>>>>>>>>>>>>>>>>>>>>

2101  atgttggcca caacattatg attattcctt gtctgtactt tagtattttt caccatttgt
      >>>>>>>>>>>>>>>>>>>>>>>>>>>>>>>>>exon 17>>>>>>>>>>>>>>>>>>>>>>>>>>>>>

2161  gaagaaacat taaaacaagt taaatggtag tgtgcggagt tttttttttct tccttctttt
      >>>>>>>>>>>>>>>>>>>>>>>>>>>>>>>>>exon 17>>>>>>>>>>>>>>>>>>>>>>>>>>>>>

2221  aaaaatggtt gtttaagact ttaacaatgg gaacccttg tgagcatgct cagtatcatt
      >>>>>>>>>>>>>>>>>>>>>>>>>>>>>>>>>exon 17>>>>>>>>>>>>>>>>>>>>>>>>>>>>>

2281  gtggagaacc aagagggcct cttaactgta acaatgttca tggttgtgat gttttttttt
      >>>>>>>>>>>>>>>>>>>>>>>>>>>>>>>>>exon 17>>>>>>>>>>>>>>>>>>>>>>>>>>>>>

2341  tttttttaaa ataaaattcc aaatgtttaa taaaaaaaaa aaaaaaaaa
      >>>>>>>>>>>>>exon 17>>>>>>>>>>>>>>
```

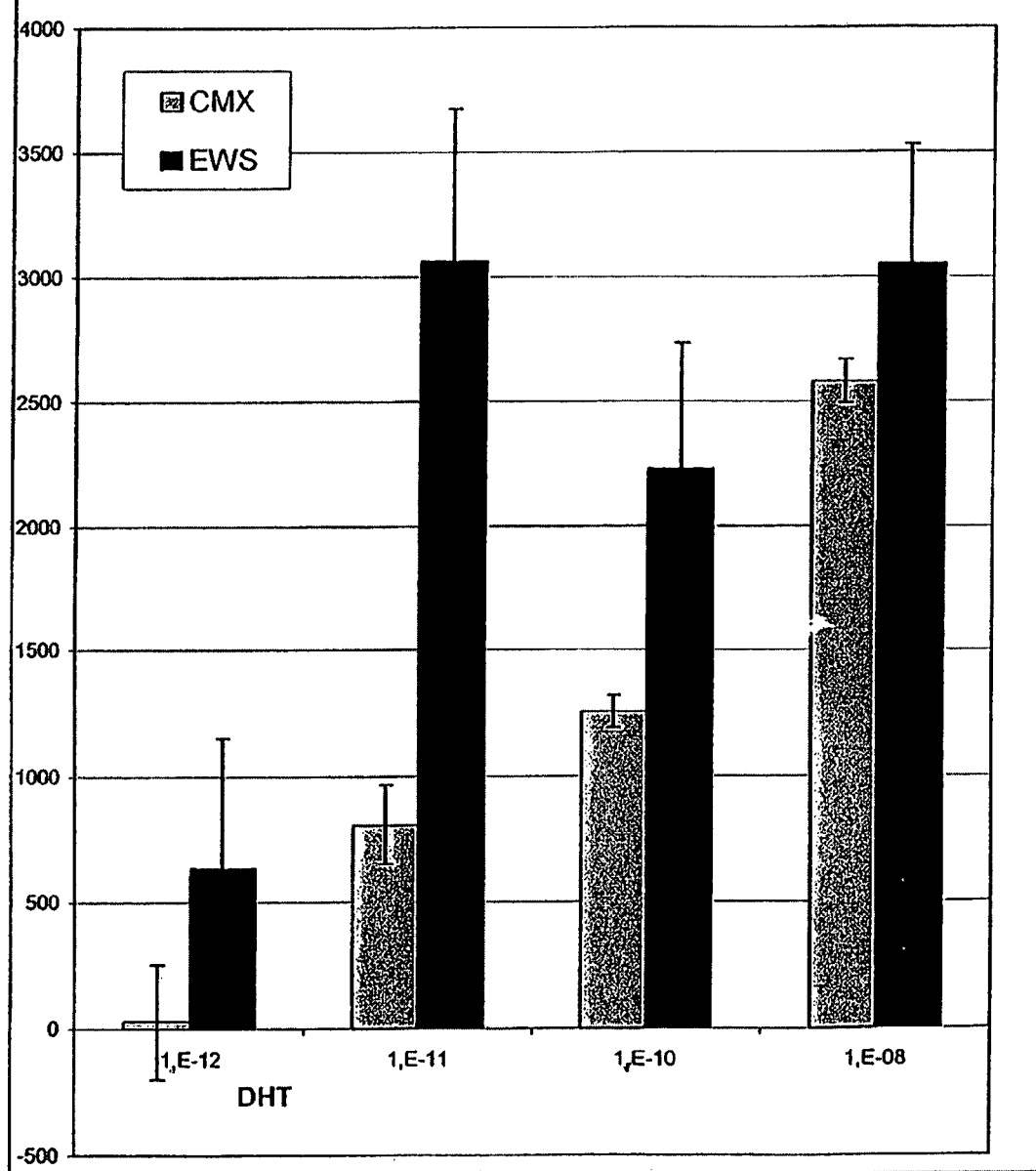

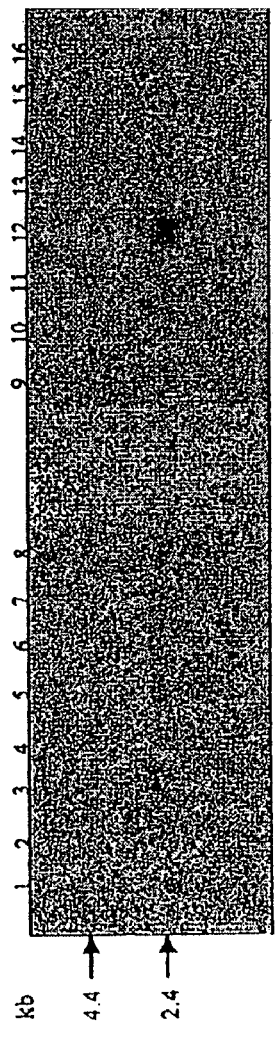
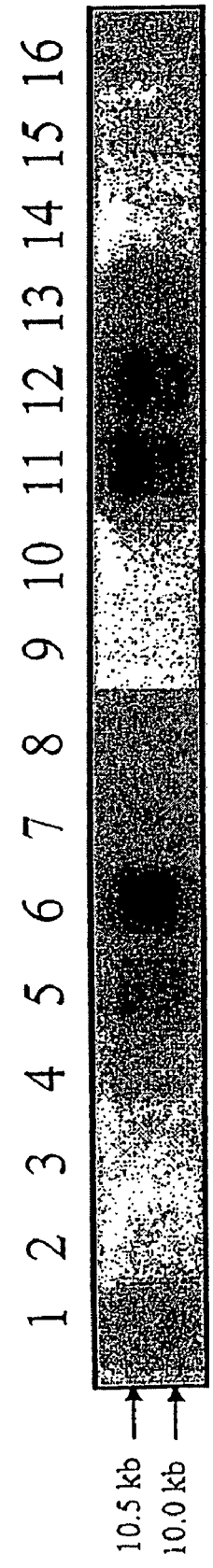
FIG. 5a
FIG. 5b

SEQUENCE LISTING

```
<160> NUMBER OF SEQ ID NOS: 7

<210> SEQ ID NO 1
<211> LENGTH: 2390
<212> TYPE: DNA
<213> ORGANISM: Homo sapiens
<220> FEATURE:
```

-continued

```
<221> NAME/KEY: CDS
<222> LOCATION: (44)..(2011)
<223> OTHER INFORMATION: EWS

<400> SEQUENCE: 1
```

| | | | | | | | | | | | | | | |
|---|---|---|---|---|---|---|---|---|---|---|---|---|---|---|
| agagggagac ggacgttgag agaacgagga ggaaggagag aaa | | | | | | | | | | atg Met 1 | gcg Ala | tcc Ser | acg Thr | 55 |
| gat Asp 5 | tac Tyr | agt Ser | acc Thr | tat Tyr | agc Ser 10 | caa Gln | gct Ala | gca Ala | gcg Ala | cag Gln 15 | cag Gln | ggc Gly | tac Tyr | agt Ser | gct Ala 20 | 103 |
| tac Tyr | acc Thr | gcc Ala | cag Gln | ccc Pro 25 | act Thr | caa Gln | gga Gly | tat Tyr | gca Ala 30 | cag Gln | acc Thr | acc Thr | cag Gln | gca Ala 35 | tat Tyr | 151 |
| ggg Gly | caa Gln | caa Gln | agc Ser | tat Tyr 40 | gga Gly | acc Thr | tat Tyr | gga Gly | cag Gln 45 | ccc Pro | act Thr | gat Asp | gtc Val | agc Ser 50 | tat Tyr | 199 |
| acc Thr | cag Gln | gct Ala | cag Gln 55 | acc Thr | act Thr | gca Ala | acc Thr | tat Tyr 60 | ggg Gly | cag Gln | acc Thr | gcc Ala | tat Tyr 65 | gca Ala | act Thr | 247 |
| tct Ser | tat Tyr 70 | gga Gly | cag Gln | cct Pro | ccc Pro | act Thr 75 | ggt Gly | tat Tyr | act Thr | act Thr | cca Pro 80 | act Thr | gcc Ala | ccc Pro | cag Gln | 295 |
| gca Ala 85 | tac Tyr | agc Ser | cag Gln | cct Pro | gtc Val 90 | cag Gln | ggg Gly | tat Tyr | ggc Gly | act Thr 95 | ggt Gly | gct Ala | tat Tyr | gat Asp | acc Thr 100 | 343 |
| acc Thr | act Thr | gct Ala | aca Thr | gtc Val 105 | acc Thr | acc Thr | acc Thr | cag Gln | gcc Ala 110 | tcc Ser | tat Tyr | gca Ala | gct Ala | cag Gln 115 | tct Ser | 391 |
| gca Ala | tat Tyr | ggc Gly | act Thr | cag Gln 120 | cct Pro | gct Ala | tat Tyr | cca Pro | gcc Ala 125 | tat Tyr | ggg Gly | cag Gln | cag Gln | cca Pro 130 | gca Ala | 439 |
| gcc Ala | act Thr | gca Ala | cct Pro 135 | aca Thr | aga Arg | ccg Pro | cag Gln | gat Asp 140 | gga Gly | aac Asn | aag Lys | ccc Pro | act Thr 145 | gag Glu | act Thr | 487 |
| agt Ser | caa Gln | cct Pro | caa Gln 150 | tct Ser | agc Ser | aca Thr | ggg Gly | ggt Gly 155 | tac Tyr | aac Asn | cag Gln | ccc Pro | agc Ser 160 | cta Leu | gga Gly | 535 |
| tat Tyr | gga Gly | cag Gln | agt Ser 165 | aac Asn | tac Tyr | agt Ser | tat Tyr | ccc Pro 170 | cag Gln | gta Val | cct Pro | ggg Gly | agc Ser 175 | tac Tyr | ccc Pro 180 | 583 |
| atg Met | cag Gln | cca Pro | gtc Val | act Thr 185 | gca Ala | cct Pro | cca Pro | tcc Ser | tac Tyr 190 | cct Pro | cct Pro | acc Thr | agc Ser | tat Tyr 195 | tcc Ser | 631 |
| tct Ser | aca Thr | cag Gln | ccg Pro 200 | act Thr | agt Ser | tat Tyr | gat Asp | cag Gln 205 | agc Ser | agt Ser | tac Tyr | tct Ser | cag Gln 210 | cag Gln | aac Asn | 679 |
| acc Thr | tat Tyr | ggg Gly 215 | caa Gln | ccg Pro | agc Ser | agc Ser | tat Tyr 220 | gga Gly | cag Gln | cag Gln | agt Ser | agc Ser 225 | tat Tyr | ggt Gly | caa Gln | 727 |
| caa Gln | agc Ser | agc Ser 230 | tat Tyr | ggg Gly | cag Gln | cag Gln | cct Pro 235 | ccc Pro | act Thr | agt Ser | tac Tyr | cca Pro 240 | ccc Pro | caa Gln | act Thr | 775 |
| gga Gly | tcc Ser | tac Tyr 245 | agc Ser | caa Gln | gct Ala | cca Pro | agt Ser 250 | caa Gln | tat Tyr | agc Ser | caa Gln | agc Ser 255 | agc Ser | agc Ser | agc Ser 260 | 823 |
| tac Tyr | ggg Gly | cag Gln | cag Gln | agt Ser 265 | tca Ser | ttc Phe | cga Arg | cag Gln | gac Asp 270 | cac His | ccc Pro | agt Ser | agc Ser | atg Met 275 | ggt Gly | 871 |
| gtt Val | tat Tyr | ggg Gly | cag Gln | gag Glu | tct Ser | gga Gly | gga Gly | ttt Phe | tcc Ser | gga Gly | cca Pro | gga Gly | gag Glu | aac Asn | cgg Arg | 919 |

```
                                                           -continued

Val Tyr Gly Gln Glu Ser Gly Gly Phe Ser Gly Pro Gly Glu Asn Arg
        280                 285                 290 agc atg agt ggc cct gat aac cgg ggc agg gga aga ggg gga ttt gat        967
Ser Met Ser Gly Pro Asp Asn Arg Gly Arg Gly Arg Gly Gly Phe Asp
            295                 300                 305 cgt gga ggc atg agc aga ggt ggg cgg gga gga cgc ggt gga atg            1015
Arg Gly Gly Met Ser Arg Gly Gly Arg Gly Gly Arg Gly Gly Met
    310                 315                 320 ggc agc gct gga gag cga ggt ggc ttc aat aag cct ggt gga ccc atg        1063
Gly Ser Ala Gly Glu Arg Gly Gly Phe Asn Lys Pro Gly Gly Pro Met
325                 330                 335                 340 gat gaa gga cca gat ctt gat cta ggc cca cct gta gat cca gat gaa        1111
Asp Glu Gly Pro Asp Leu Asp Leu Gly Pro Pro Val Asp Pro Asp Glu
                345                 350                 355 gac tct gac aac agt gca att tat gta caa gga tta aat gac agt gtg        1159
Asp Ser Asp Asn Ser Ala Ile Tyr Val Gln Gly Leu Asn Asp Ser Val
            360                 365                 370 act cta gat gat ctg gca gac ttc ttt aag cag tgt ggg gtt gtt aag        1207
Thr Leu Asp Asp Leu Ala Asp Phe Phe Lys Gln Cys Gly Val Val Lys
        375                 380                 385 atg aac aag aga act ggg caa ccc atg atc cac atc tac ctg gac aag        1255
Met Asn Lys Arg Thr Gly Gln Pro Met Ile His Ile Tyr Leu Asp Lys
    390                 395                 400 gaa aca gga aag ccc aaa ggc gat gcc aca gtg tcc tat gaa gac cca        1303
Glu Thr Gly Lys Pro Lys Gly Asp Ala Thr Val Ser Tyr Glu Asp Pro
405                 410                 415                 420 ccc act gcc aag gct gcc gtg gaa tgg ttt gat ggg aaa gat ttt caa        1351
Pro Thr Ala Lys Ala Ala Val Glu Trp Phe Asp Gly Lys Asp Phe Gln
                425                 430                 435 ggg agc aaa ctt aaa gtc tcc ctt gct cgg aag aag cct cca atg aac        1399
Gly Ser Lys Leu Lys Val Ser Leu Ala Arg Lys Lys Pro Pro Met Asn
            440                 445                 450 agt atg cgg ggt ggt ctg cca ccc cgt gag ggc aga ggc atg cca cca        1447
Ser Met Arg Gly Gly Leu Pro Pro Arg Glu Gly Arg Gly Met Pro Pro
        455                 460                 465 cca ctc cgt gga ggt cca gga ggc cca gga ggt cct ggg gga ccc atg        1495
Pro Leu Arg Gly Gly Pro Gly Gly Pro Gly Gly Pro Gly Gly Pro Met
    470                 475                 480 ggt cgc atg gga ggc cgt gga gga gat aga gga ggc ttc cct cca aga        1543
Gly Arg Met Gly Gly Arg Gly Gly Asp Arg Gly Gly Phe Pro Pro Arg
485                 490                 495                 500 gga ccc cgg ggt tcc cga ggg aac ccc tct gga gga gga aac gtc cag        1591
Gly Pro Arg Gly Ser Arg Gly Asn Pro Ser Gly Gly Gly Asn Val Gln
                505                 510                 515 cac cga gct gga gac tgg cag tgt ccc aat ccg ggt tgt gga aac cag        1639
His Arg Ala Gly Asp Trp Gln Cys Pro Asn Pro Gly Cys Gly Asn Gln
            520                 525                 530 aac ttc gcc tgg aga aca gag tgc aac cag tgt aag gcc cca aag cct        1687
Asn Phe Ala Trp Arg Thr Glu Cys Asn Gln Cys Lys Ala Pro Lys Pro
        535                 540                 545 gaa ggc ttc ctc ccg cca ccc ttt ccg ccc ccg ggt ggt gat cgt ggc        1735
Glu Gly Phe Leu Pro Pro Pro Phe Pro Pro Pro Gly Gly Asp Arg Gly
    550                 555                 560 aga ggt ggc cct ggt ggc atg cgg gga gga aga ggt ggc ctc atg gat        1783
Arg Gly Gly Pro Gly Gly Met Arg Gly Gly Arg Gly Gly Leu Met Asp
565                 570                 575                 580 cgt ggt ggt ccc ggt gga atg ttc aga ggt ggc cgt ggt gga gac aga        1831
Arg Gly Gly Pro Gly Gly Met Phe Arg Gly Gly Arg Gly Gly Asp Arg
                585                 590                 595
```

```
ggt ggc ttc cgt ggt ggc cgg ggc atg gac cga ggt ggc ttt ggt gga      1879
Gly Gly Phe Arg Gly Gly Arg Gly Met Asp Arg Gly Gly Phe Gly Gly
            600                 605                 610 gga aga cga ggt ggc cct ggg ggg ccc cct gga cct ttg atg gaa cag      1927
Gly Arg Arg Gly Gly Pro Gly Gly Pro Pro Gly Pro Leu Met Glu Gln
        615                 620                 625 atg gga gga aga aga gga gga cgt gga gga cct gga aaa atg gat aaa      1975
Met Gly Gly Arg Arg Gly Gly Arg Gly Gly Pro Gly Lys Met Asp Lys
    630                 635                 640 ggc gag cac cgt cag gag cgc aga gat cgg ccc tac tagatgcaga           2021
Gly Glu His Arg Gln Glu Arg Arg Asp Arg Pro Tyr
645                 650                 655 gaccccgcag agctgcattg actaccagat ttatttttta aaccagaaaa tgttttaaat    2081
ttataattcc atatttataa tgttggccac aacattatga ttattccttg tctgtacttt    2141 agtattttc accatttgtg aagaaacatt aaaacaagtt aaatggtagt gtgcggagtt     2201
tttttttctt ccttcttta aaaatggttg tttaagactt taacaatggg aaccccttgt     2261
gagcatgctc agtatcattg tggagaacca agagggcctc ttaactgtaa caatgttcat    2321
ggttgtgatg tttttttttt ttttttaaaa taaaattcca aatgtttaat aaaaaaaaaa    2381
aaaaaaaaa                                                            2390

<210> SEQ ID NO 2
<211> LENGTH: 656
<212> TYPE: PRT
<213> ORGANISM: Homo sapiens

<400> SEQUENCE: 2

Met Ala Ser Thr Asp Tyr Ser Thr Tyr Ser Gln Ala Ala Ala Gln Gln
1               5                   10                  15

Gly Tyr Ser Ala Tyr Thr Ala Gln Pro Thr Gln Gly Tyr Ala Gln Thr
            20                  25                  30

Thr Gln Ala Tyr Gly Gln Gln Ser Tyr Gly Thr Tyr Gly Gln Pro Thr
        35                  40                  45

Asp Val Ser Tyr Thr Gln Ala Gln Thr Thr Ala Thr Tyr Gly Gln Thr
    50                  55                  60

Ala Tyr Ala Thr Ser Tyr Gly Gln Pro Pro Thr Gly Tyr Thr Thr Pro
65                  70                  75                  80

Thr Ala Pro Gln Ala Tyr Ser Gln Pro Val Gln Gly Tyr Gly Thr Gly
                85                  90                  95

Ala Tyr Asp Thr Thr Thr Ala Thr Val Thr Thr Thr Gln Ala Ser Tyr
            100                 105                 110

Ala Ala Gln Ser Ala Tyr Gly Thr Gln Pro Ala Tyr Pro Ala Tyr Gly
        115                 120                 125

Gln Gln Pro Ala Ala Thr Ala Pro Thr Arg Pro Gln Asp Gly Asn Lys
    130                 135                 140

Pro Thr Glu Thr Ser Gln Pro Gln Ser Ser Thr Gly Gly Tyr Asn Gln
145                 150                 155                 160

Pro Ser Leu Gly Tyr Gly Gln Ser Asn Tyr Ser Tyr Pro Gln Val Pro
                165                 170                 175

Gly Ser Tyr Pro Met Gln Pro Val Thr Ala Pro Pro Ser Tyr Pro Pro
            180                 185                 190

Thr Ser Tyr Ser Ser Thr Gln Pro Thr Ser Tyr Asp Gln Ser Ser Tyr
        195                 200                 205

Ser Gln Gln Asn Thr Tyr Gly Gln Pro Ser Ser Tyr Gly Gln Gln Ser
    210                 215                 220
```

```
Ser Tyr Gly Gln Gln Ser Ser Tyr Gly Gln Gln Pro Thr Ser Tyr
225                 230                 235                 240

Pro Pro Gln Thr Gly Ser Tyr Ser Gln Ala Pro Ser Gln Tyr Ser Gln
            245                 250                 255

Gln Ser Ser Ser Tyr Gly Gln Gln Ser Ser Phe Arg Gln Asp His Pro
                260                 265                 270

Ser Ser Met Gly Val Tyr Gly Gln Glu Ser Gly Gly Phe Ser Gly Pro
            275                 280                 285

Gly Glu Asn Arg Ser Met Ser Gly Pro Asp Asn Arg Gly Arg Gly Arg
            290                 295                 300

Gly Gly Phe Asp Arg Gly Gly Met Ser Arg Gly Arg Gly Gly Gly
305                 310                 315                 320

Arg Gly Gly Met Gly Ser Ala Gly Glu Arg Gly Gly Phe Asn Lys Pro
                325                 330                 335

Gly Gly Pro Met Asp Glu Gly Pro Asp Leu Asp Leu Gly Pro Pro Val
            340                 345                 350

Asp Pro Asp Glu Asp Ser Asp Asn Ser Ala Ile Tyr Val Gln Gly Leu
            355                 360                 365

Asn Asp Ser Val Thr Leu Asp Asp Leu Ala Asp Phe Phe Lys Gln Cys
370                 375                 380

Gly Val Val Lys Met Asn Lys Arg Thr Gly Gln Pro Met Ile His Ile
385                 390                 395                 400

Tyr Leu Asp Lys Glu Thr Gly Lys Pro Lys Gly Asp Ala Thr Val Ser
                405                 410                 415

Tyr Glu Asp Pro Pro Thr Ala Lys Ala Ala Val Glu Trp Phe Asp Gly
            420                 425                 430

Lys Asp Phe Gln Gly Ser Lys Leu Lys Val Ser Leu Ala Arg Lys Lys
            435                 440                 445

Pro Pro Met Asn Ser Met Arg Gly Gly Leu Pro Pro Arg Glu Gly Arg
            450                 455                 460

Gly Met Pro Pro Pro Leu Arg Gly Gly Pro Gly Pro Gly Gly Pro
465                 470                 475                 480

Gly Gly Pro Met Gly Arg Met Gly Gly Arg Gly Gly Asp Arg Gly Gly
                485                 490                 495

Phe Pro Pro Arg Gly Pro Arg Gly Ser Arg Gly Asn Pro Ser Gly Gly
            500                 505                 510

Gly Asn Val Gln His Arg Ala Gly Asp Trp Gln Cys Pro Asn Pro Gly
            515                 520                 525

Cys Gly Asn Gln Asn Phe Ala Trp Arg Thr Glu Cys Asn Gln Cys Lys
530                 535                 540

Ala Pro Lys Pro Glu Gly Phe Leu Pro Pro Pro Phe Pro Pro Pro Gly
545                 550                 555                 560

Gly Asp Arg Gly Arg Gly Gly Pro Gly Gly Met Arg Gly Gly Arg Gly
            565                 570                 575

Gly Leu Met Asp Arg Gly Gly Pro Gly Gly Met Phe Arg Gly Gly Arg
            580                 585                 590

Gly Gly Asp Arg Gly Gly Phe Arg Gly Gly Arg Gly Met Asp Arg Gly
            595                 600                 605

Gly Phe Gly Gly Gly Arg Arg Gly Gly Pro Gly Pro Pro Gly Pro
            610                 615                 620

Leu Met Glu Gln Met Gly Gly Arg Arg Gly Gly Arg Gly Gly Pro Gly
625                 630                 635                 640
```

```
Lys Met Asp Lys Gly Glu His Arg Gln Glu Arg Arg Asp Arg Pro Tyr
                645                 650                 655
```

```
<210> SEQ ID NO 3
<211> LENGTH: 20
<212> TYPE: DNA
<213> ORGANISM: artificial sequence
<220> FEATURE:
<223> OTHER INFORMATION: Primer

<400> SEQUENCE: 3
gattacgcta gcttgggtgg                                              20

<210> SEQ ID NO 4
<211> LENGTH: 21
<212> TYPE: DNA
<213> ORGANISM: artificial sequence
<220> FEATURE:
<223> OTHER INFORMATION: Primer

<400> SEQUENCE: 4
gttgaagtga acttggcggg g                                            21

<210> SEQ ID NO 5
<211> LENGTH: 27
<212> TYPE: DNA
<213> ORGANISM: artificial sequence
<220> FEATURE:
<223> OTHER INFORMATION: Primer

<400> SEQUENCE: 5
gggtcgacgg acgttgagag aacgagg                                      27

<210> SEQ ID NO 6
<211> LENGTH: 33
<212> TYPE: DNA
<213> ORGANISM: artificial sequence
<220> FEATURE:
<223> OTHER INFORMATION: Primer

<400> SEQUENCE: 6
gggaattctg cggggtctct gcatctagta ggg                               33

<210> SEQ ID NO 7
<211> LENGTH: 18
<212> TYPE: DNA
<213> ORGANISM: artificial sequence
<220> FEATURE:
<223> OTHER INFORMATION: Primer

<400> SEQUENCE: 7
gcttgggtgg tcatatgg                                                18
```

METHODS FOR DETERMINING HORMONAL EFFECTS OF SUBSTANCES USING EWING SARCOMA PROTEIN AND ANDROGEN RECEPTOR

CROSS-REFERENCE

This disclosure contains subject matter in common with U.S. provisional application Ser. No. 60/465,692, filed Apr. 25, 2003.

REFERENCE TO SEQUENCE LISTING TABLES

A sequence listing appended hereinbelow lists seven sequences for proteins and nucleic acids. The first sequence designated SEQ ID NO: 1 is for DNA, which codes for the EWS protein of SEQ ID NO: 2. The sequence designated SEQ ID NO: 2 is for EWS protein with 656 amino acids. The sequence designated SEQ ID NO: 3 is an artificial DNA sequence with 20 base pairs. SEQ ID NO: 4 is an artificial DNA sequence with 21 base pairs. SEQ ID NO: 5 is an artificial DNA sequence with 27 base pairs. SEQ ID NO: 6 is an artificial DNA sequence with 33 base pairs and SEQ ID NO: 7 is an artificial DNA sequence with 18 base pairs. The sequence designated SEQ ID NO: 8 is for the human androgen receptor protein with 918 amino acids.

A copy of the written sequence listing in computer readable form (CRF) is also provided on an accompanying floppy disk. The content of the sequence listing information recorded in CRF on the floppy disk is identical to the written sequence listings appended hereinbelow and includes no new matter.

BACKGROUND OF THE INVENTION

1. Field of the Invention

The invention relates to methods for determining hormonal effects of substances and a method for determining interference in co-modulation mechanisms of nuclear receptors (NR). Further the invention also relates to methods of using Ewing sarcoma protein (EWS) or of EWS derivatives and nucleic acids, which code for them.

2. Description of the Related Art

When substances are judged for possible pharmaceutical applications they are usually tested for contingent hormonal activity, especially for possible androgenic or anti-androgenic activity. Knowledge of those hormonal effects, especially androgenic or anti-androgenic effects, is important for judging possible side effects of administration of these pharmaceutically active substances. For example to test hormonal action of substances methods are used, in which the ability of the substances to bind to hormone receptors and to activate transcription activity is measured.

Knowledge regarding hormonal effects of substances is of interest not only for pharmaceuticals, but also for non-pharmaceutical substances, since many substances in the environment can have androgenic or anti-androgenic or estrogenic or anti-estrogenic activity in part of the population. Possibly undesired injurious effects may occur.

It is especially difficult to identify and characterize effects mediated by steroid hormones, since the signal cascade and networks, which control the hormone mediated transcription regulation, are especially complex. The reason for that is connected with the very similar structure of the DNA target sequences, to which the different steroid hormone receptors bind after ligand activation. This causes the nuclear receptors to turn on a targeted response to interaction with special cofactors, which, among other things, increase the specificity of the receptor-mediated transcription activity.

For identification of substances, which affect certain hormone induced signal paths, thus test systems and methods are required, which can detect the function of individual components of the cellular signal network for mediation of steroidal effects.

There is thus a need for a method, which obtains information regarding the hormonal effects of substances to be tested so that a statement regarding those effects can be made in a reliable, sensitive, simple, economic and rapid manner.

SUMMARY OF THE INVENTION

It is thus an object of the present invention to provide a method for obtaining information regarding the hormonal effects of substances to be tested in a reliable, sensitive, simple, economic and rapid manner.

This object and, others which will be made more apparent hereinafter, is attained by a method for determining hormonal effects of substances, which comprises the following steps:

a) bringing a test substance into contact with Ewing sarcoma protein (EWS) or a derivative of Ewing sarcoma protein and with a nuclear receptor (NR) or a derivative of the nuclear receptor; and b) determining the effect of the test substance on binding of Ewing sarcoma protein (EWS) or a derivative of it with the nuclear receptor or its derivative; or c) determining the effect of the test substance on ligand-induced activity of the nuclear receptor.

The term "derivative" of a protein and/or polypeptide (such as EWS) can mean in the context of the present invention any of the following: e.g. variants of the protein and/or polypeptide obtained by amino acid deletion, substitution, insertion, inversion, addition or exchange. Those protein derivatives are especially preferred, which have the ability to influence the activity of other proteins, e.g. of unchanged proteins or polypeptides, or at least to bind to them (functional derivatives).

The invention is based on the surprising knowledge that Ewing sarcoma protein and derivatives of it (henceforth designated "EWS" in the following description) has the ability to interact with nuclear receptors (and/or their derivatives) and modulate their activity.

The super-family of nuclear receptors (NRs), which includes about 50 different proteins, consists of a group of related transcription factors, which control reaction to certain specific ligands, e.g. hormones, like the transcription of a respective target gene. This family can be subdivided into several subfamilies according to certain characteristics, for example dimerization status, type of ligands or structure of the DNA reacting element (Beato et al., 2000, Human Reproduct. Update 6, 225–236). A characteristic feature of nuclear receptors is the corresponding structures of functional domains (marked A to F). These domains consist of a highly variable, only slightly conservative N-terminal region with an autonomous constitutive activation function (AF-1), a well-conserved DNA-binding domain (DBD), which is responsible for recognition of special DNA-binding elements and consists of two zinc finger motifs, a variable hinge domain and a multifunctional conserved C-terminal ligand-binding domain (LBD) with a dimerization-dependent and ligand-dependent transactivation function (AF-2). This is followed by a region located at the most remote C-terminal, whose function is not known and which is absent in certain receptors. These receptors are, for example, PR (progesterone receptor), PPAR (peroxisome proliferator-activator receptor) and RXR (retinoid X receptor) (Mangelsdorf & Evans, 1995, Cell 83, 841–850; Robyr et al., 2000, Mol. Endocrinol. 14, 329–347). It was demonstrated for some nuclear receptors (for example AR) that the N-terminal region is able to interact with the C-terminal region (Brinkmann, et al, 1999, J. Steroid Biochem. and Mol. Biol. 69, 307–313). Steroid hormone receptors, such as estrogen receptors (ER), progesterone receptors (PR), glucocorticoid receptors (GR), mineralocorticoid receptors (MR) and androgen receptors (AR) bind steroid ligands, such as the progestins, estrogens, glucocorticoids, mineralocorticoids and androgens, all of which are derived from pregnenolone. The ligand binding to the receptor activates the receptor and controls the expression of the corresponding target genes.

EWS is known as a proto-oncogene of Ewing sarcoma and other neoplasms, such as clear cell sarcoma of tendons and aponeuroses, and of small and round cell desmoplastic intraabdominal tumors and extraskeletal chondrosacroma (Delattre, O., Zucman, J., Plougastel, B., Desmaze, C., Melot, T., Peter, M., Kovar, H., Joubert, I., dejong, P., Roubleau, G. Aurias, A., and Thomas, G., 1992, Nature 359, pp. 162–165; Zucman, J., Delattre, O., Desmaze, C., Epstein, A. L., Stenman, G., Speleman, F., Fletchers, C. D., Aurias, A., and Thomas, G., Nature Genet. 4, pp. 341–345; Gerald, W. L., Rosai, J. and Ladanyi, M., 1995, Proc. Natl. Acad. Sci. USA 92, pp. 1028–1032; Laballe, Y., Zucman, J., Stenman, G., Kindblom, L. G., Knight, J., Turc-Carel, C., Dockhorn-Dworniszak, B., Mandahl, N., Demaze, C., Peter, M., Aurias, A., Delattre, O., and Thomas, G., 1995, Hum. Mol. Genet. 4, pp.2219–2226). The EWS gene locus is rearranged in all these tumors so that the amino acid end (N-terminus) of the protein is fused with a DNA binding domain of FLI1, ERG1, ATF1 or WT1. This N-terminal end of the fusing protein holds the ESW exons 1–7 or 1–8 or 1–9. If the break point lies between exon 7 and exon 8, the EWS portion of the protein arising by the fusion has no correspondence with the androgen receptor binding domain. In contrast if the break point lies between exon 8 and 9 or 9 and 10, only 5 and/or 20 amino acids of both oncogenic EWS fusion proteins correspond with the EWS portion, which contains the androgen receptor binding domain. Thus the rearranged EWS fusion proteins have lost the ability to bind to the androgen receptors.

During analysis of thymus RNA by means of RT-PCR an EWS variant (EWS1-c) was found in which 17 amino acids are missing. Evidently it is a splice variant, since all necessary consensus sequences were present at the neighboring sites between the introns and exons. The result was a shortening of exon 15 (exon 15b). According to the prior art other splice variants are known. One (Ohno, T., Ouchida, M., Lee, L., Gatalica, Z., Rao, V. N., and Reddy, E. S., 1994, Oncobene 9, pp. 3087–3097) is an about 200-bp-shorter EWS transcript (EWS1-b). It was found in resting lymphocytes or in lymphocytes stimulated by phytohemagglutinin (PHA). Exons 8 and 9 are omitted from the EWS1-b. Another variant (Melot, T., Dauphinot, L., Sevenet, N., Radvanyi, F., Delattre, O. (2001), Eur. J. Biochem. 268, pp. 3483–3489) contains an additional exon 4' between exons 4 and 5 and is characterized as a brain-specific isoform.

EWS belongs to a group of RNA-binding proteins, which are described as implicated in RNA synthesis and processing. Besides that however only little is known about the physiological function of somatic wild-type EWS. Especially the prior art did not known that EWS has the ability to bind to nuclear receptors (NR) and modulate their activity, whereby it is part of the class of nuclear receptor co-modulators.

An *E. Coli* strain designated *Escherichia Coli* EWS-10 CMX was deposited in the German collection of Microorganisms and Cell Cultures GmbH (DSMZ) under the Nr. DSM 15417 on Jan. 24, 2003. *Escherichia Coli* EWS-10 CMX contains the full length EWS-cDNA, which was used in the method according to the invention.

The so-called co-modulators are a class of proteins, which act as bridging modules between the transcription initiating complex and the nuclear receptors in activation (co-activation) and repression (co-repression)(McKenna, et al, 1999, Endocr. Rev. 20, pp. 321–347). A co-activator must be able to amplify the receptor function and to interact directly with the activation domains of the nuclear receptors in the presence of an agonist. It must also interact with the basal transcription apparatus and subsequently it must not increase the basal transcription activity by itself. Most co-modulators interact with the AF-2 domains of the nuclear receptors with the help of one or more LXXLL-motives (NR-boxes). However a few co-modulators were described which interact with other NR regions (Ding, et al., 1998, Mol. Endocrinol., 12, pp. 302–313). Furthermore many co-modulators were identified, which interact in similar ways with several different nuclear receptors.

The methods according to the invention can be performed both in vitro (also e.g. as purely biochemical or biophysical assays, in solution or in suitable solid matrices, etc) and also partially or entirely in cellular systems. One skilled in the art is knowledgeable regarding these test systems.

Preferably at least one of the method steps of the invention is performed in a cellular system, since the effects of the steroid-mediated transcription activity are produced especially well in the physiological context of cells. Both primary and established eukaryotic cells are especially suitable for use in the method according to the invention. The use of established cell lines permits an especially good reproducibility and economy. In contrast, the use of primary cells largely avoids mutation and clone-selected conditioned cell culture artifacts. Prostate cells, nerve cells, glia cells, fibroblasts, blood cells, osteoblasts, osteoclasts, hepatocytes, epithelial cells or muscle cells are especially suitable.

The hormonal effects determined here (i.e. identification, quantification or characterization) can be both of an activating and also inhibiting nature and can also relate to other steps of nuclear receptor action besides activation on receptor-co-modulator binding, e.g. ligand-induced transactivation and also nuclear localization of the nuclear receptor.

Preferred embodiments of the method include the following steps:

a) first cells, which express EWS or a derivative of it and a nuclear receptor or a derivative of it, are exposed to the test substance;

b) the protein-protein interaction or the protein-protein-DNA interaction is measured to determine the effect of the test substance on the interaction between the receptor or its derivative and EWS or its derivative.

Expression of one or both components interacting with each other (EWS/derivative, on the one hand, and NR/derivative, on the other hand) can occur in cells from nature or as a result of transient or stable transfection with suitable expression vectors. The selection of suitable cell types and if necessary vector systems is a standard procedure known to those skilled in the art. For example pCMX or pSG5 is suitable for expression in eukaryotic systems.

The measurement of protein-protein interaction between receptor and/or its derivatives and EWS or its derivatives or the protein-protein-DNA interaction of the above-described components with DNA target sequences occurs by procedures known to those skilled in the art. For this purpose techniques, such as the two hybrid system, co-immunoprecipitation, GST pull down assays, FRET analyses and ABCD assays and/or gel retardation assays are suitable for analysis of protein-protein-DNA interactions.

In preferred embodiments of the method according to the invention the following steps are performed:

a) cells, which express EWS or a derivative of it and a nuclear receptor or a derivative of it and are transfixed with a reporter gene construct, are exposed to ligands of the nuclear receptor and the substance to be tested;

b) transcription activity of the nuclear receptor is determined by measuring the reporter gene activity; and c) the transcription activity ascertained by performing steps a) and b) is compared with that when the test substance is not present.

Reporter genes are genes or gene fragments, which code for as simple as possible gene fragments, e.g. photometically by dye reactions. Frequently used reporter genes are the gene for β-galactosidease, the gene for alkali phosphatase, the gene for chloramphenicol-acetyltransferase, the gene for catechol-dioxygenase, the gene for "green" or "blue fluorescent protein" as well as different luciferase genes, which can cause cell luminescence. The activity of the transcription factor and/or the cascade can be determined with the aid of the expressed gene product by a series of suitable control elements, e.g. a promotor-enhancer sequence, which is under control of a certain transcription factor or a certain signal transduction cascade.

This sort of reporter gene is conventionally introduced into the cells in a suitable vector in connection with an interesting promotor-enhancer sequence. All known nuclear receptor target sequences—depending on the nuclear receptor to be analyzed—are suitable for analysis of the steroidal activity of substances. For example the MMTV-luciferase vector, which is used for measurement of androgenic activity of substances, is suitable for use as a vector in the method according to the invention.

Substances with a hormonal effect, preferably an androgenic/anti-androgenic effect, are then detected by an increased or reduced expression of the reporter gene in comparison to experimental assays without addition of the substance to be tested.

Besides wild type EWS, EWS derivatives, and especially functional EWS derivatives, which have kept the ability to modulate the activity of at least one nuclear receptor, especially the androgen receptor, or at least to bind to it (in a not negligible manner detected by suitable methods—e.g. protein-protein interaction assays like EMSA; which one skilled in the can differentiate) are suitable in the method according to the invention. The same goes for NR derivatives: Those derivatives are also preferred, which have maintained the ability to be modulated or at least bound by EWS or its functional derivatives.

EWS and EWS-coded nucleic acids are already known in the prior art. Preferably an EWS coded by the nucleic acid according to Seq. ID No. 1, or its derivative (especially a functional derivative), are suitable for use in the method according to the present invention. An EWS derivative, which has amino acids 319 to 656 of the sequence described Seq. ID No. 1, especially a fragment containing these amino acids, is especially preferred.

The invention accordingly relates to the use of ESW or its derivatives for identification and characterization of substances that influence the activity of a nuclear receptor.

Beyond this the present invention relates to the use of nucleic acids with at least 70% homology to Seq. ID No. 1 or to sequence region 8 to 2032 or sequence region 1000 to 2011 of Seq. ID No. 1 for identification and characterization of substances, which influence the activity of nuclear receptors. These types of nucleic acids are cloned in expression cassettes of suitable expression vectors, especially eukaryotic expression vectors.

The term "nucleic acids with at least 70% homology to Seq. ID No. 1" is understood to mean the entire range between 70% and 100% homology (also complete correspondence with Seq. ID No. 1). The selection of nucleic acids suitable for the respective purpose in the stated homology range is within the ability of those of ordinary skill in the art. The determination of the nucleic acid homology occurs in a way that is familiar to those of ordinary skill in the art. For this purpose different computer programs, for example BLAST, BLAST-2, ALIGN or MEGALIGN (DNASTAR), are known to those skilled in the art.

The methods according to the invention or the uses of the above-described proteins and/or nucleic acids are suitable especially for analysis of hormonal effects of substances at androgen receptors, estrogen receptors (α and β), progesterone receptors, glucocorticoid receptors, mineralocorticoid receptors, thyroid gland hormone receptors, vitamin-D receptors, peroxisome proliferator-activated receptors, retinic acid receptors, retinoid-X receptors or orphan receptors. Because of the especially good characterizing action of EWS and/or EWS derivatives at the androgen receptor, it is employed in especially preferred embodiments of the method according to the invention.

Beyond this EWS can be used as a clinical indicator of androgen-conditioned illnesses. Relevant androgen-conditioned illnesses include e.g. prostate cancer, baldness, acne or hypogonadism, and androgen-resistant syndromes, such as testicular feminization. These illnesses are probably based on defects in the co-modulator mechanism between androgen receptor and EWS. Thus measurement of the relative rates of AR and EWS is a plausible diagnostic possibility for patients with this sort of trouble. This is possible using a quantitative measurement method for relative amounts of both molecules in the target tissues in the respective patients.

A further aspect of the invention accordingly relates to the use of a nucleic acid with at least 70% homology to Seq. ID No. 1, to use of sequence ranges 8 to 2032 or 1000 to 2011 of Seq. ID No. 1 or to use of an antibody, which is directed against a protein coded by these nucleic acids, to diagnose illnesses which accompany a dysfunction of nuclear receptor activity, preferably androgen receptor activity.

One such use advantageously occurs in a method for determining interference with the co-modulation mechanism between androgen receptor and EWS, in which the cellular concentrations or tissue concentrations of androgen receptor and EWS are measured. Especially radio immunoassays, ELISAs, immunodyeing, quantitative RT-PCRs, Northern blot or Western blot are among the different techniques suitable for this purpose known to those skilled in the art.

These sorts of measurements of the relative rates of androgen receptor versus EWS have the theoretical basis that androgen-resistance syndrome is based on an interference of the equilibrium between AR- and EWS-prevalence in the target cells. Too much EWS could lead to an oversensitivity of the androgen receptor system, so that it reacts to molecules, which normally have no androgenic effect. Absence of EWS or EWS function can lead to low or reduced sensitivity at all levels of androgen resistance.

Furthermore it is possible to construct a PCR assay with the help of a suitable EWS-cDNA primer, with which mutations of the normal DNA sequence may be detected in certain patients or transcripts for the Northern Blot Assay and/or a DNA for In-situ-hybridization assays may be generated.

The detection of too much EWS in patients speaks for the use of means or measures for lowering the EWS level. This can occur, for example by means of antisense nucleic acids relative to EWS or EWS derivatives or by similar techniques to reduce the EWS titer in the respective patients under clinical conditions. This could also be achieved by molecules, which are in a position to inhibit the interaction between AR and EWS.

In contrast should a patient have too low a level of EWS, one could administer EWS-cDNA, EWS-protein or EWS DNA to him in order to increase the titer of active EWS in this manner. Another aspect of the invention relates accordingly to the use of the above-described EWS or EWS-derivative-coding nucleic acids or EWS proteins or EWS derivatives, which are coded by those nucleic acids, for therapies for illnesses dependent on dysfunction of nuclear receptor activity.

BRIEF DESCRIPTION OF THE SEVERAL VIEWS OF THE DRAWING

The objects, features and advantages of the invention will now be illustrated in more detail with the aid of the following description of the preferred embodiments, with reference to the accompanying figures in which:

FIG. 3 shows the nucleotide sequence SEQ ID NO: 1 and the EWS exons of the cDNA coding the EWS protein with the amino acid sequence SEQ ID NO: 2;

FIG. 4 is a graphical illustration showing relative co-activation of the AR signal in SH-SY5Y cells with CMX and EWS respectively; and FIGS. 5a and 5b are respective illustrations showing the distribution of EWS transcripts and AR transcripts in various tissues.

EXAMPLES

Example 1

Oligonucleoties Employed:

Primer for the PCR Amplification of Library Inserts:
Act2c5050Eco: gattacgctagcttgggtgg (SEQ. ID NO: 3)
Act24939Xho: gttgaagtgaacttggcgggg (SEQ. ID NO: 4)

Primer for Amplification of EWS-cDNA in Full Length:
EWS-8-Sal: gggtcgacggacgttgagagaacgagg (SEQ ID NO: 5)

cESW-c2032-Eco: gggaattctgcggggtctcgcatctagtaggg (SEQ ID NO: 6)

Sequence Primer:
XII-139a1: gcttgggtggtcatatgg (SEQ ID NO: 7)

Vectors Used:
pACT2 (Genbank Access Number U29899) for the library;
pGBT9 derivative for the probes: pGBT9rev and pGBT(+1)rev (Roder, K. H.; Wolf, S. S.; Schweizer, M., 1996, Analytical Biochemistry, 241, pp. 260–62);
pCR2.1 Topo-Vector (Invitrogen Co) for coding of the PCR fragment;
CMX Vector for expression of mammalian cells;
PAluc for reporter gene assay (contains the MMTV promoter and a Luciferase reporter gene; A. Cato Co.);
pSG5AR (pSG5 with the human genes for the androgen receptor; Gene bank access number AAA51775).

Organisms Used:
Yeast strain: Y187 and PJ69-2A
E-Coli Strain: DH5α
Mammalian Cells: SH-SY5Y (German Collection of Microorganisms and Cell Cultures GmbH (DSMZ): DSM ACC209);
PC3 (American Type Culture Collection (ATCC): CRL-1435; and
PC3AR: with pSG5AR stabile transfixed PC3 (A. Cato Co., Karlsruhe, Germany)

To identify new co-modulators of the androgen receptor a Human cDNA library ("Matchmaker" of Clonetech; Nr. HY4028AH) from fetal brain was screened with three different fragments of the androgen receptor (AR) as probe with the help of a yeast-two hybrid system.

Figure 1:
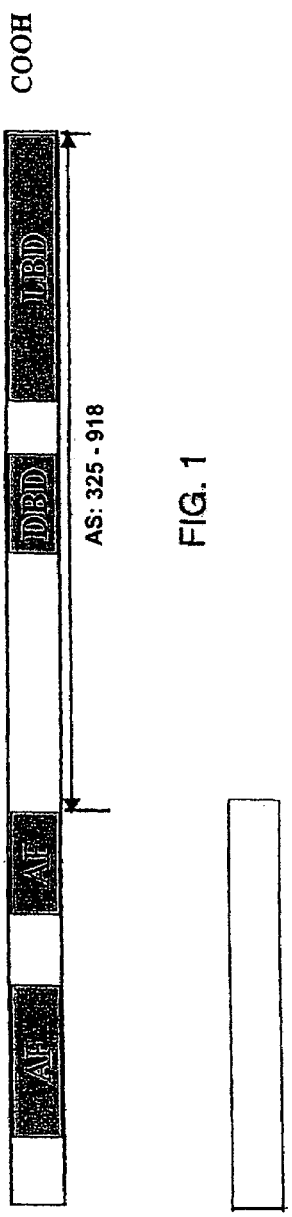
FIG. 1 is a diagrammatic illustration of the gene for the androgen receptor (AR) and the AR2 fragment, in which the androgen receptor fragment (AR2) is designated as AS: 325–918; the activation domain with AF, DNA binding domains, with DBD; ligand binding domains with LBD; activation domains with AD and binding domains with BD.

For this purpose pSG5AR vector, which contains the cDNA for the human androgen receptor protein of SEQ ID NO: 8 (Genbank AAA51775), was cleaved with the help of Endonuclease PstI, so that three different AR-DNA fragments were produced. The shortest of these fragments (AR4) coded for the N-terminus of the receptor (AS 1–56), the middle length fragment (AR3) coded for the middle part with the activation domain (AS 57–324) and the longest fragment (AR2) coded for the C-terminus (AS 325–918) with the DNA and ligand binding domains (DBD and LBD; compare with FIG. 1). AR2 was cloned in the pGBT9(+1) rev vector, since it was previously linearized with the help of endonuclease PstI.

Subsequently the transformation of the pGBT vector, which contains the AR fragment, occurs in the yeast strain PJ69-2A. The positive transformant (Trp+) was incubated with a cDNA library obtained from fetal brain according to the instructions from the manufacturer (Human Multiple Tissue cDNA (MTC), Panel II of Clontech Cat. Nr. K1421-1). 3×10$^6$ clones were screened in accordance with the instructions from the manufacturer (Clontech). The positive clones were selected and tested for their β-galactosidase activity according to the instructions of the manufacturer (Clontech). The inserts of the blue colonies originating from the library were increased directly from the yeast cells by means of PCR using the primer Act2c5050Eco and Act 2-4939Xho.

The PCR products were further analyzed by gel electrophoresis for its length after scission and by means of cleavage with MspI. At least one example of each restriction fragment pattern was sequenced using XII-139a1 as sequence primer. The sequences were compared with Incyte of Genbank or Databank.

Figure 2:
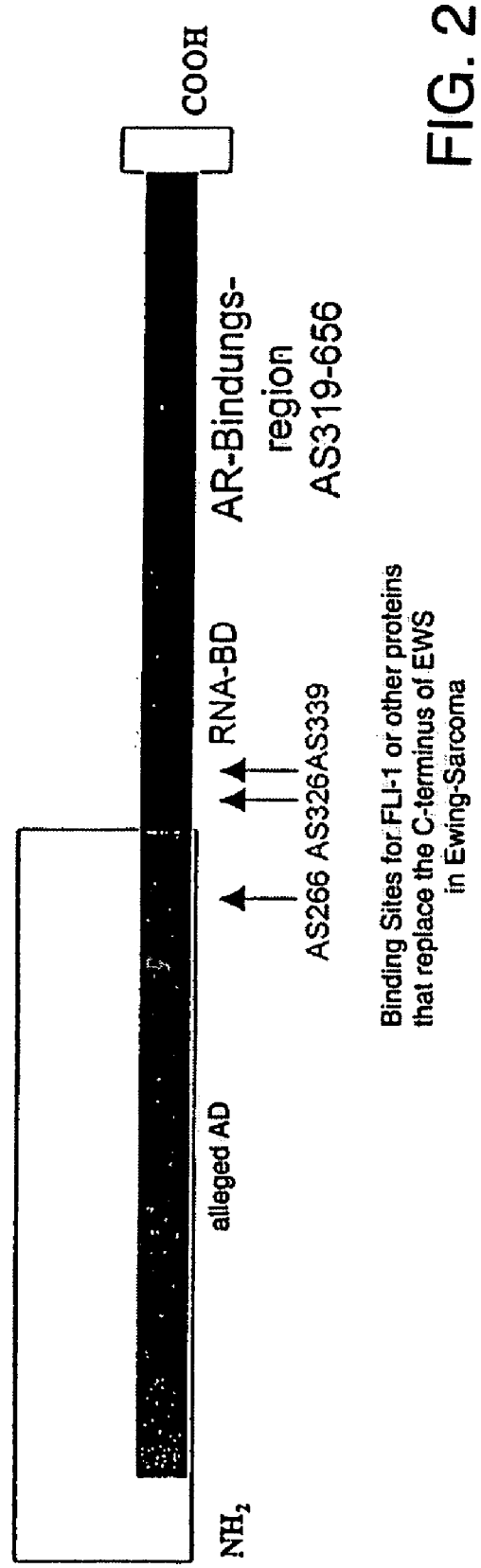
FIG. 2 is a diagrammatic illustration of the gene for the Ewing sarcoma protein (EWS), in which blue shows the RNA binding domain, dark red, the androgen receptor binding domain AS 319–656.

One of the many identified inserts had a length of 1500 bp and could be identified by sequencing and sequence comparison with Databank NCBJ as coding for the C-terminal part of human EWS (AS 319–656) (see FIG. 2 and amino acid sequence in FIG. 3).

FIG. 3 shows the nucleotide sequence for the cDNA coding for human EWS protein together with the derived amino acid sequence. Exons 1 to 17 are shown. The letters printed in bold face characterize the fragment, which is to be found in the yeast two hybrid system and binds to the androgen receptor section AS 325 to AS 919. The sequence regions absent in the splice variant EWS1-b (underlined with a solid line) or EWS1-c (underlined with a dotted line) are underlined in FIG: 3.

EWS in its full length was amplified or increased by means of PCR using EWS-8-Sal primer and cEWS-c2032-Eco primer as well as thymus-cDNA or spleen-cDNA of Clontech. The complete coding region of the transcript was isolated from spleen and the variant with exon 15B instead of exon 15 was isolated from thymus. The amplified cDNA was then cloned with EcoRI and Sal I in the expression cassette of mammalian expression vector CMX.

FIG. 4 shows the co-activation of the AR signal in SY-SY5Y cells. 1 µg MMTV-Luciferase and 0.75 µg pSG5AR plasmid were supplied to each reaction chamber of a six-reaction-chamber reaction plate. Each of these six mixtures was transferred to four cavities of a microtiter plate and measured there. The error bars show the standard deviation SD. The measured values were obtained by subtracting the corresponding control values without DHT.

As the bar graph shown in FIG. 4 shows, after transient transfection in SH-SY5Y cells EWS is able to induce a strong co-activation of the androgen receptor signal action, especially at low androgen concentrations of $10^{-12}$ to $10^{-10}$ mol. For this purpose SH-SY5Y cells in reaction plates with six reaction cavities were co-transfected with 0.75 µg of a vector, which contained the cDNA for the human androgen receptor (pSG5AR), 1.5 µg of reporter gene construct pAHluc, which contains the MMTV promoter for the Luciferase gene, and 1 µg of EWS-CMX vector. The transfection occurred using lipofectin of Gibeo BRC according to the instructions of the manufacturer. Twenty-four hours after the transfection the cells were incubated over night with different androgen amounts. The cells were subjected to lysis with a commercial lysis buffer and the luciferase activity was measured in a Lumistar luminometer of BMG Lab Technologies. The EWS-CMX Luciferase activity was compared with the control activity (empty CMX vector). The mixture in each cavity was measured in four cavities of a microtiter plate. The control values of the substance were subtracted without DHT. The standard deviation was shown with vertical lines indicating the range on the bars in FIG. 4.

The tissue distribution of human EWS in normal human tissue is apparent from the distribution of EWS-transcripts shown in FIG. 5a with the aid of autoradiography. For this purpose a random priming of an EWS-cDNA fragment, which coded for amino acids 244–656 of EWS, and a marking with $^{32}$P-α-dATP and the Klenow fragment, according to the MEGAPRIME® Marking system, took place according to the instructions of the manufacturer. The marked fragment was purified with a Nick column (Pharmacia) according to the instructions of the manufacturer and was hybridized with Human Blot and Human Northern Blot (MTN) Nr. 7760-1 and Nr. 7759-1 of Clontech. The blots were hybridized with the probe, washed, transferred to a film and developed. As is apparent from the results shown in FIG. 5a, EWS-RNA is predominantly expressed in testicles. Different tissues contain different amounts of EWS.

FIG. 5b shows the tissue distribution of human androgen receptor transcripts in normal human tissues. Tissues numbered 1 to 16 show the relative amount of human androgen receptor in the following tissues respectively: heart, brain, placenta, lung, liver, skeletal muscle, kidney, pancreas, spleen, thymus, prostate, testicles, ovaries, small intestine, large intestine and peripheral leucocytes. From FIGS. 5a and 5b one can ascertain the normal expression of both these proteins in the tissues.

FIG. 5a shows the tissue distribution of EWS transcript (Northern Blot MTN of Clontech). A random priming of the EWS-cDNA fragment of the manufacturer (Amersham), which codes for the amino acids 244 to 656, and marking with $^{32}$P-α-dATP and the Klenow fragment took place according to the instructions of the manufacturer. The blots were hybridized with the probe, washed, transferred to a film and developed.

The disclosure in German Patent Application 103 09 280.3 of Mar. 4, 2003 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a method for determination of hormonal effects of substances, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. An in vitro method of determining if a test substance has an androgenic or anti-androgenic effect, said method comprising the steps of:
   a) exposing cells, which recombinantly express Ewing sarcoma protein (EWS) of SEQ ID NO: 2 or a fragment of said Ewing sarcoma protein comprising amino acids 319–656 and which express human androgen receptor (AR) or a fragment of said human androgen receptor comprising amino acids 325–918 of SEQ ID NO: 8, to said test substance to be tested in vitro; and
   b) measuring protein-protein interaction or protein-protein-DNA interaction in order to determine the effect of the test substance on binding of said Ewing sarcoma protein (EWS) or said fragment of said Ewing sarcoma protein with said human androgen receptor (AR) or said fragment of said human androgen receptor;
   wherein the androgenic or anti-androgenic effect of the test substance is indicated by an increase or decrease in the binding determined in step b) in the presence of the test substance in comparison to the binding without the test substance present.

2. The method as defined in claim 1, wherein said cells are eukaryotic cells.

3. The method as defined in claim 1, wherein said cells are eukaryotic cells selected from the group consisting of prostate cells, nerve cells, glia cells, fibroblasts, blood cells, osteoblasts, osteoclasts, hepatocytes, epithelial cells, and muscle cells.

4. The method as defined in claim 1, wherein said measuring to determine the effect of the test substance comprises two hybrid system techniques, co-immuno-precipitation techniques, GST pull-down assays, FRET analyses, ABGD assays, or gel retardation assays.

5. The method as defined in claim 1, wherein said human androgen receptor comprises amino acids 1 to 918 of SEQ ID NO: 8.

6. An in vitro method of determining if a test substance has an androgenic or anti-androgenic effect, said method comprising the steps of:
   a) exposing cells, which recombinantly express Ewing sarcoma protein (EWS) of SEQ ID NO: 2, which express human androgen receptor (AR), and which are transfected with a reporter gene construct, to said test substance to be tested in vitro together with a ligand of said human androgen receptor; and
   b) measuring reporter gene activity to determine transcription activity of the human androgen receptor (AR) in the presence of said test substance; and
   c) comparing the transcription activity determined in step b) with transcription activity determined by repeating steps a) and b) in the absence of said test substance;
   wherein the androgenic or the anti-androgenic effect of said test substance is indicated if said transcription activity measured in step b) is different from said transcription activity determined in the absence of the test substance in step c).

7. The method as defined in claim 6, wherein said cells are eukaryotic cells.

8. The method as defined in claim 6, wherein said cells are eukaryotic cells selected from the group consisting of prostate cells, nerve cells, glia cells, fibroblasts, blood cells, osteoblasts, osteoclasts hepatocytes, epithelial cells, and muscle cells.

9. The method as defined in claim 6, wherein said human androgen receptor comprises amino acids 1 to 918 of SEQ ID NO: 8.

10. An in vitro method of determining if a test substance has an androgenic or anti-androgenic effect, said method comprising the steps of:
    a) exposing cells, which recombinantly express Ewing sarcoma protein (EWS) of SEQ ID NO: 2 and which express human androgen receptor (AR), to said test substance to be tested in vitro; and
    b) measuring protein-protein interaction or protein-protein-DNA interaction in order to determine the effect of the test substance on binding of said Ewing sarcoma protein (EWS) with said human androgen receptor (AR);
    wherein the androgenic or anti-androgenic effect is indicated by an increase or decrease respectively in the binding measured in step b) in the presence of the test substance in comparison to the binding without the test substance present.

* * * * *